United States Patent [19]

Ferrer

[11] Patent Number: 4,883,426

[45] Date of Patent: Nov. 28, 1989

[54] DENTAL IMPLEMENT FOR FLUID ASPIRATION AND TISSUE RETRACTION

[76] Inventor: Euler R. Ferrer, 410 N. Bristol "C", Santa Ana, Calif. 92703

[21] Appl. No.: 215,407

[22] Filed: Jul. 5, 1988

Related U.S. Application Data

[63] Continuation-in-part of Ser. No. 128,219, Dec. 3, 1987.

[51] Int. Cl.[4] .............................................. A61L 17/04
[52] U.S. Cl. ......................................... 433/91; 433/93
[58] Field of Search ............................... 433/91, 92, 93

[56] References Cited

U.S. PATENT DOCUMENTS 3,090,122  5/1963  Erickson ................................ 433/93
3,333,340  8/1967  Boisvert ................................. 433/91

FOREIGN PATENT DOCUMENTS 1949517  4/1971  Fed. Rep. of Germany ........ 433/93

Primary Examiner—Robert Peshock
Attorney, Agent, or Firm—Gary Appel

[57] ABSTRACT

A disposable, plastic dental implement is provided for enabling both the aspiration of fluids from a patient's mouth and the retracting of soft tissues in the patient's mouth. The implement is a slender, elongate member having a hollow tubular portion having a suction end and a connection end for connecting the member to a conventional suction tube. Relatively narrow, first and second, longitudinally-extending fins project sidewardly from opposite, lower, side regions of said tubular portion. These fins, which are substantially uniform in width and thickness, extend around a suction end of the tubular member to abut one another. A region of the fins around the suction end of tubular portion are curved downwardly to form an arcuate, tissue-retraction tip at the suction end of the member. Preferably, the width of the fins is less than the outside diameter of the tubular portion at its connection end. The suction end of the tubular portion is cut at a slant and has at least two opposing recesses which enable suction to be broken between the member and soft tissues of the patient's mouth should the need arise.

23 Claims, 2 Drawing Sheets

DENTAL IMPLEMENT FOR FLUID ASPIRATION AND TISSUE RETRACTION

This application is a continuation-in-part application of Ser. No. 07/128,219, filed on December 3, 1987.

BACKGROUND OF THE INVENTION:

1. Field of the Invention:

The present invention relates generally to the field of dental implements and, more particularly, to dental implements for evacuating fluids and other materials from a dental patient's mouth.

2. Discussion of the Prior Art:

It is a matter of common experience and knowledge that when dental work is being performed in a patient's mouth—whether the work is the cleaning of teeth; the drilling of teeth and installation of fillings, crown and the like; or the performing of oral surgery—it is necessary that the working area of the mouth be kept free of fluids and debris. These fluids may include saliva, blood, liquid used with drilling, and/or rinsing liquids, and the debris may be drilling "dust", broken pieces of teeth, and/or pieces of fillings. It is also important, for the patient's comfort, to keep fluids from accumulating in the patient's mouth so that the fluids and debris are not swallowed and the patient can, if necessary, breath through his or her mouth.

Commonly, a suction device is periodically used to keep the dental work area clean and the patient's mouth relatively clear of fluids and debris. Such suction devices typically comprise a relatively rigid—and often disposable—suction tube, which is connected to a long flexible hose, which is, in turn, connected to a vacuum source.

Although it is a common procedure, while a dentist is working on a tooth, for a dental assistant to manipulate the suction tube so as to maintain a clean work area and enable good visibility for the dentist of the tooth being worked on, this procedure is not always convenient for the dentist. For example, the dental assistant may be unable to anticipate the dentist's moves in the patient's mouth and may thus be unable to keep the end of the suction tube out of the dentist's way. As a consequence, the dentist may prefer to do the evacuation of fluids and debris from the patient's mouth himself or herself. Also, a dental assistant may not always be available to manipulate a suction tube, but may be needed for such other routine and important tasks as processing X-rays, preparing filling compounds, and cleaning dental instruments.

In order for a dentist to work on a patient's tooth, for example, to drill into the tooth in preparation for installing a filling or to perform some other dental operation, such as rootcanal, it is usually necessary for the dentist to use an instrument to push or pull soft tissue regions of the patient's mouth away from the work area. This may be necessary to provide a more unrestricted view of the work area or to prevent accidental injury to the patient's mouth. Sometimes, a dental mirror may be used for retracting tissue or other specialized dental implements may be used. However, problems result when both a substantial amount of tissue retraction and fluid evacuation is needed. In such instances, the working area of a patient's mouth may become crowded with dental implements to an extent that the dentist's task becomes very difficult to perform. Moreover, it may be necessary for the dentist to frequently and repeatedly shift between tissue retraction and fluid evacuation implements, thereby requiring a longer time for the dental task being performed and adding to the patient's discomfort. Also, the possibility is increased for making an error in the dental work being performed when the work area in the patient's mouth is congested with dental implements or when the dentist is required to repeatedly shift between dental implements.

It is, therefore, a principal objective of the present invention to provide a single dental implement which combines the features of both a generally conventional fluid aspirator or evacuation device and a soft tissue retraction device. As a result, a dentist, dental hygienist, dental assistant, or the like can shift between the evacuation of fluids from a patient's mouth and the retracting of soft tissues from a patient's mouth without the necessity for changing dental implements each time. Dental tasks are thereby made more efficient and the risk of error is reduced, as is, in general, patient discomfort.

SUMMARY OF THE INVENTION:

According to the present invention, there is provided a dental implement for the aspiration of fluids from a patient's mouth and for the retracting of soft tissues in the patient's mouth. The dental implement comprises a slender, elongate member having a hollow tubular portion and rigid, first and second, longitudinally-extending fins which project sidewardly from opposite, lower, side regions of the tubular portion. The fins, which are preferably relatively narrow and of uniform width and thickness, extend around a suction end of the tubular member to join one another. It is preferred that the region of the fins around the suction end of the tubular member be at least slightly curved downwardly to form an arcuate, tissue-retraction tip adjacent the suction end of the tubular portion. According to a preferred embodiment of the invention, the first and second fins extend a substantial distance from the suction end of the tubular portion towards the connection end thereof and are of a substantially uniform width and thickness, with the width of each fin being less than the outside diameter of the tubular portion at the connection end thereof.

The connection end of the tubular member is preferably round in transverse cross-section and an upper region of the tubular portion adjacent the suction end thereof may be substantially flat so that the tubular portion is thinner at the suction end than at the connection end.

Further, in accordance with the preferred embodiment, the suction end of the tubular portion is formed having an open end surface which is generally planar and is at an angle relative to a plane orthogonal to the longitudinal axis of the member so that the open end surface at the flat upper region of the tubular portion is closer to the connection end than are other regions of the open end surface. Also, the open end surface of the tubular portion suction end is formed having at least one recess enabling suction to be broken between the member and soft tissues of a patient's mouth when suction is applied to the dental implement and the suction end of the member inadvertently contacts a soft tissue region of the patient's mouth.

To prevent injury to a patient's mouth by the dental implement, all exposed edges of the tubular portion and the first and second fins are smoothly rounded so that there are no sharp exposed edges, and upper and lower surfaces of the first and second fins are smoothly flared into the outer surface of the tubular portion.

It is preferred that the dental implement be constructed (for example, molded) from an inexpensive plastic material so that the implement is disposable and can be discarded after use with any patient.

BRIEF DESCRIPTION OF THE DRAWINGS:

The present invention can be more readily understood from the following detailed description, when taken in conjunction with the accompanying drawings, in which.

When the same elements and features are shown in more than one FIG., they are given the same reference numbers in such FIGS.

Figure 1:
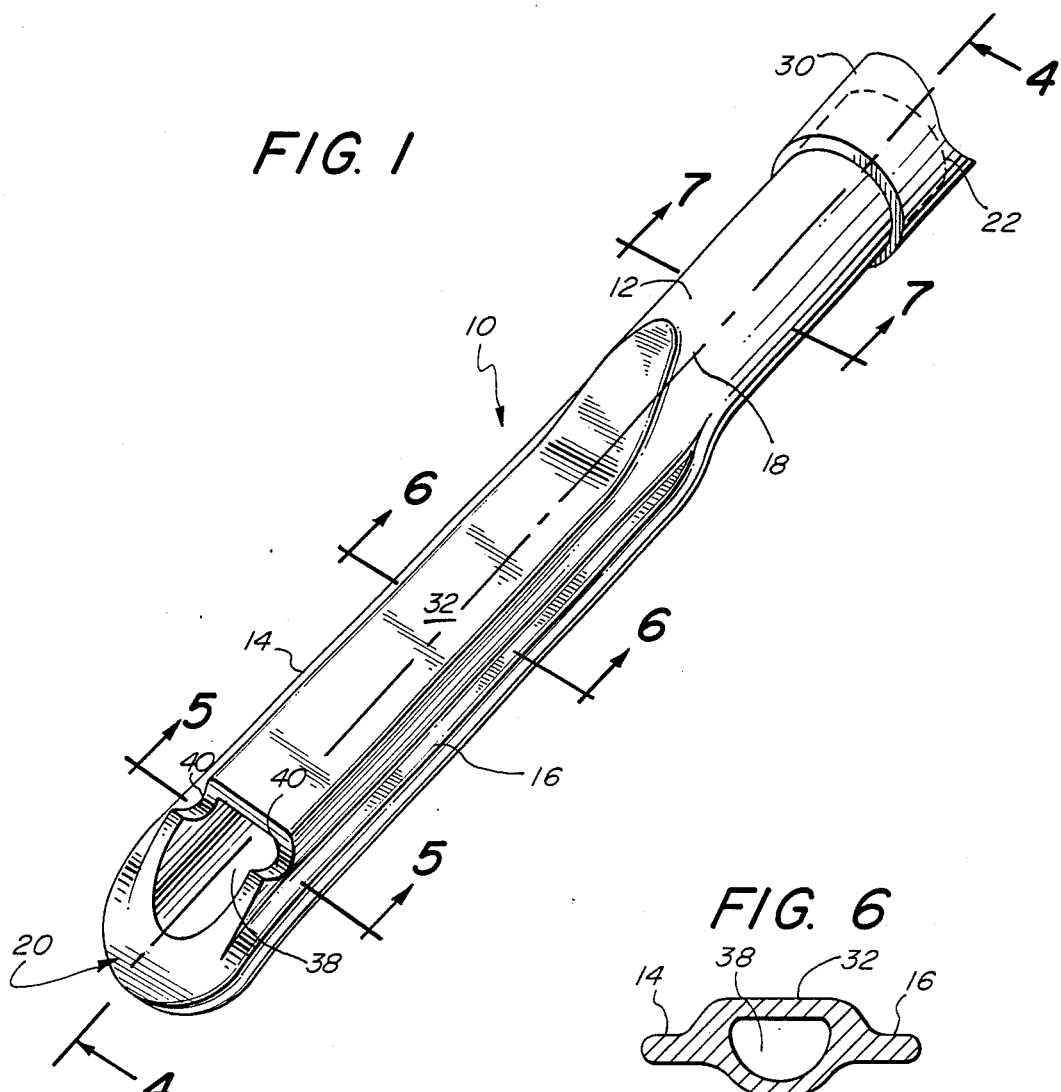
FIG. 1 is a perspective drawing (looking from the top) of a combination fluid suction and tissue retraction, dental implement, in accordance with a preferred embodiment of the present invention, showing the general configuration of the implement.

DESCRIPTION OF THE PREFERRED EMBODIMENT:

There is shown in FIG. 1 a dental implement 10, in accordance with a preferred embodiment of the present invention, which can be used for the dual purposes of aspirating or withdrawing fluids from a dental patient's mouth and for retracting soft tissues in the patient's mouth. Consequently, a dentist or other dental professional can have the benefit of two separate instruments in only one instrument.

As is more particularly described below, dental implement 10 is relatively long and slender—compared to the size of a typical dental patient's mouth, and may, by way of example and with no limitations being thereby intended or implied, be about five inches in overall length and less than about three-quarters on an inch in overall width. Therefore, implement 10 is easy and convenient to handle and to use in even relatively small mouths. By way of comparison, dental implement 10 is about the length and width of a small, conventional tongue depressor used in the medical and dental professions.

Figure 7:
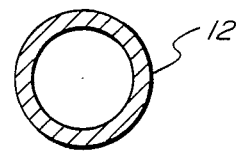
Figure 2:
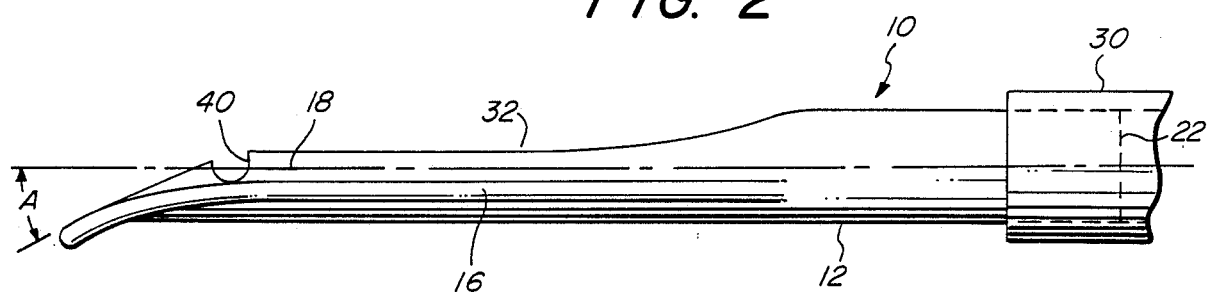
FIG. 2 is a side view of the dental implement shown in FIG. 1, showing, in particular, a downwardly curved, tissue retraction region of the implement adjacent to the suction end thereof, and showing a notched region of the suction end of the implement, by means of which suction between the implement and soft tissue regions of a patient's mouth can readily be broken.
Figure 4:
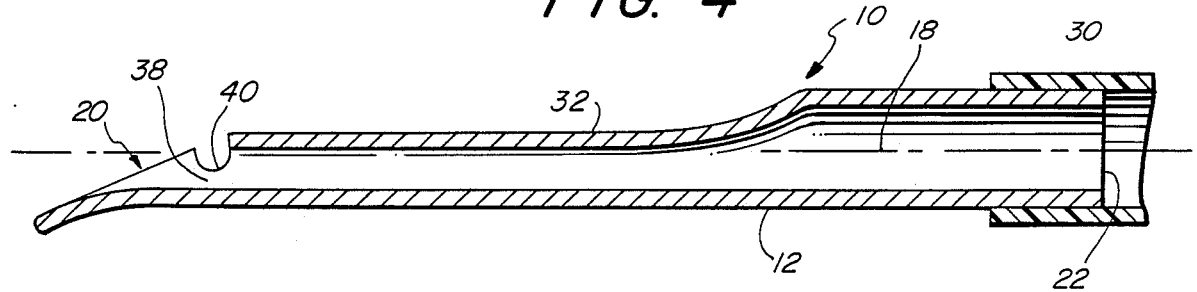
FIG. 4 is a longitudinal, cross-sectional view, taken along line 4—4 of FIG. 1, showing the internal construction of the dental implement.
Figure 3:
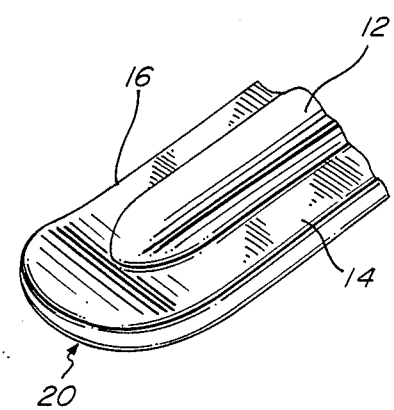
FIG. 3 is partial perspective drawing of the implement of FIG. 1 looking at the suction end of the implement from the under side.

More specifically, dental implement 10 is an elongate member, which comprises generally a tubular portion 12 and first and second side fins 14 and 16. As shown in FIGS. 1 and 2, tubular portion 12 extends along a longitudinal axis 18 of implement 10 almost the entire length of the implement. Tubular portion 12 has a suction end 20 and a connection end 22, the latter being circular in transverse cross-section (FIG. 7) and being sized to fit into a preexisting suction tube 30 (FIGS. 1, 2, and 4).

First and second fins 14 and 16 project sidewardly from opposite, lower side regions of tubular portion 12, as is shown in FIGS. 1-3, 5, and 6, and preferably extend a substantial portion—for example, about two-thirds—of the entire length of implement 10 (FIGS. 1 and 2) from suction end 20. As is shown, fins 14 and 16 extend around suction end 20 of tubular portion 12 and meet at a vertical plane through longitudinal axis 18. In this manner, first and second fins 14 and 16 can be considered as forming a single, U-shaped fin which extends down both sides and around suction end 20 of tubular portion 12. Although first and second fins 14 and 16 may be straight along sides of tubular portion 12, it is preferred that they be slightly curved, as best seen in FIG. 2.

Figure 6:
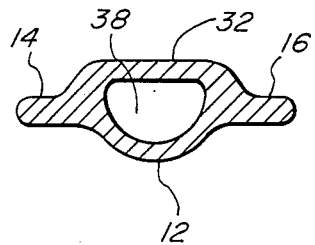
FIG. 6 is a transverse cross-sectional view, taken along line 6—6 of FIG. 1, showing the configuration of the dental implement in a central region thereof; and, FIG. 7 is a transverse cross-sectional drawing, taken along line 7—7 of FIG. 1, showing the configuration of the dental implement near the connection end thereof.
Figure 5:
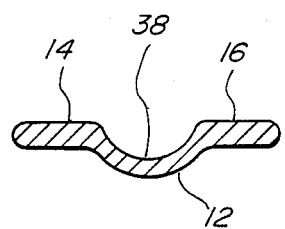
FIG. 5 is a transverse cross-sectional view, taken along line 5—5 of FIG. 1, showing the configuration of the dental implement near the suction end thereof.

It is also preferred that first and second fins 14 and 16 be of substantially uniform thickness and width over their entire length and around suction end 20 of tubular portion, and that the width of the fins be less than the diameter of tubular portion 12 at connection end 22 (FIG. 6). The thickness of first and second fins 14 and 16 is such that the fins are not sharp and it is preferred that exposed edges of the fins be smoothly rounded so that dental implement 10 has no sharp edges or corners which might cut or injure a patient's mouth. It is further preferred, as shown in FIGS. 5 and 6, that first and second fins 14 and 16 be smoothly flared into tubular portion 20 so that, for example, there are no crevices in which debris may be caught or in which a patient's tooth might wedge.

To better enable the retraction of soft tissue by dental implement 10, it is preferred that a region 30 of first and second fins 14 and 16 around suction end 22 of tubular portion 12 be curved downwardly so that the tangent to the curve is at an angle "A", relative to longitudinal axis 18 (FIG. 2), which is preferably between about 15 and 45 degrees, and which is more preferably about 27 degrees. This downward curvature of dental implement 10 at the suction tip provides somewhat of a "hook" by which the retraction of soft tissue in a patient's mouth may be better controlled.

As seen in FIGS. 1, 2, and 4-7, dental implement 10 is generally tapered from connection end 22 of tubular portion 12 to suction end 20. Such tapering, which makes dental implement more convenient to use, takes up less space in a patient's mouth, and enables better visibility for the dentist or other dental personnel manipulating the implement. Preferably, as best seen in FIGS. 2 and 4, the tapering of implement 10 is accomplished by flattening upper regions of tubular portion 12 progressively more and more from about the start of first and second fins 14 and 16 to suction end of the tubular portion, a relatively flat upper surface region 32 being thereby provided. As a result of this progressive flattening of tubular portion 12, a central aperture 36 through the tubular portion changes from a circular shape at connection end 22 (FIG. 7) to about a semicircular shape (FIG. 6) near suction end 20. Although flattened surface region 34 is, as shown, curved in a very shallow "S" shape, it may alternatively be completely flat, as would be provided by a uniform taper of tubular member 12.

Because of the taper of tubular portion 12 toward suction end 20, a suction opening 38 (FIGS. 1 and 4) at the suction end is at a slanting angle which is about equal to angle "A" (FIG. 2).

When using dental implement 10 as a fluid extraction implement, it may—and probably will—sometimes occur that the implement is moved so that suction opening 38 is blocked by soft tissue, such as the cheek or tongue, in the patient's mouth. With suction applied, it may be difficult to pull the implement loose, at least without causing discomfort, and perhaps even pain, to the patient. To substantially prevent such blockage of suction opening 38, a pair of opposing notches or recesses 40 are formed in suction end 20 of tubular portion 12. Even in the event that suction opening 38 still becomes blocked by soft tissue in the patient's mouth, a slight rolling or twisting movement of implement 10 about longitudinal axis 18 should be sufficient to break the suction and enable movement of the implement.

It is preferred, for sanitary reasons, that the dental implement be constructed of a relatively inexpensive, yet strong plastic, such as PVC, polystyrene, or polycarbonate, so as to be disposable after use with a patient. However, since all dental implements used in a patient's mouth are sterilized after use, it is within the scope of the invention that dental implement 10 be alternatively constructed of a surgical type of steel, such as stainless steel.

Although there is described above a specific arrangement of a combination fluid aspirating and tissue retracting dental implement in accordance with the present invention for the purpose of illustrating the manner in which the invention can be used to advantage, it is to be appreciated that the invention is not limited thereto. Accordingly, any and all variations and modifications which may occur to those skilled in the art are to be considered to be within the scope and spirit of the invention as defined by the appended claims.

What is claimed is:

1. A dental implement for the aspiration of fluids from a patient's mouth and for the retracting of soft tissues in said patient's mouth, the dental implement comprising a slender, elongate and substantially straight member having:
    (a) a hollow tubular portion having a longitudinal axis and having a suction end and a connection end remote from the suction end for enabling the member to be connected to a suction tube or the like; and,
    (b) first and second, longitudinally extending fins which project sidewardly from opposite, lower, side regions of said tubular portion, said fins being of substantially uniform width and being rigid and relatively narrow and extending along a substantial length of said tubular member from the suction end thereof and extending around the suction end of the tubular portion so as to join one another at a vertical plane through said longitudinal axis.

2. The dental implement as claimed in claim 1, wherein portions of the first and second fins around the suction end of the tubular portion are at least slightly curved downwardly so as to form an arcuate, tissue-retraction tip of said member relatively adjacent the suction end of the tubular portion.

3. The dental implement as claimed in claim 1, wherein said first and second fins are of a substantially uniform thickness.

4. The dental implement as claimed in claim 1, wherein the width of each of the first and second fins is less than the outside diameter of the tubular portion at the connection end thereof.

5. The dental implement as claimed in claim 1, wherein the connection end of the tubular member is round in transverse cross-section and wherein an upper region of the tubular portion adjacent the suction end thereof is substantially flat so that the tubular portion is thinner at the suction end than at the connection end.

6. The dental implement as claimed in claim 5, wherein the suction end of the tubular portion is formed having an open end surface which is generally planar and is at an angle relative to a plane orthogonal to said longitudinal axis so that said open end surface at the flat upper region of the tubular portion is closer to said connection end than are other regions of said open end surface.

7. The dental implement as claimed in claim 6, wherein the open end surface of the tubular portion suction end is formed having at least one recess enabling suction to be broken between said member and soft tissues of the patient's mouth.

8. The dental implement as claimed in claim 1, wherein all exposed edges of the tubular portion and the first and second fins are smoothly rounded so that there are no sharp exposed edges to cut a patient's mouth.

9. The dental implement as claimed in claim 1, wherein upper and lower surfaces of the first and second fins are smoothly flared into the outer surface of the tubular portion.

10. The dental implement as claimed in claim 1, wherein the member is constructed of a molded plastic material.

11. A dental implement for the aspiration of fluids from a patient's mouth and for the retracting of soft tissues in said patient's mouth, the dental implement comprising a slender, elongate and substantially straight member having:
    (a) a hollow tubular portion having a longitudinal axis and having a suction end and a connection end remote from the suction end for enabling the member to be connected to a suction tube or the like; and,
    (b) first and second, longitudinally extending fins which project sidewardly from opposite, lower, side regions of said tubular portion, said fins being of substantially uniform width and being rigid and relatively narrow and extending along a substantial length of said tubular portion from the suction end thereof and extending around the suction end of the tubular portion so as to join one another at a vertical plane through said longitudinal axis, portions of the first and second fins around the suction end of the tubular portion being curved downwardly so as to form an arcuate, tissue-retraction tip of said member relatively adjacent to the suction end of the tubular portion.

12. The dental implement as claimed in claim 11, wherein the width of each of the first and second fins is less than the outside diameter of the tubular portion at the connection end thereof.

13. The dental implement as claimed in claim 11, wherein the connection end of the tubular member is round in transverse cross-section and wherein an upper region of the tubular portion adjacent the suction end thereof is substantially flat so that the tubular portion is thinner at the suction end than at the connection end.

14. The dental implement as claimed in claim 13, wherein the suction end of the tubular portion is formed having an open end surface which is generally planar and is at an angle relative to a plane orthogonal to said longitudinal axis so that said open end surface at the flat upper region of the tubular portion is closer to said connection end than are other regions of said open end surface.

15. The dental implement as claimed in claim 14, wherein the open end surface of the tubular portion suction end is formed having at least one recess to enable suction to be broken between said member and soft tissues of the patient's mouth.

16. The dental implement as claimed in claim 11, wherein all exposed edges of the tubular portion and the first and second fins are smoothly rounded so that there are no sharp edges to cut a patient's mouth, and wherein upper and lower surfaces of the first and second fins are smoothly flared into the outer surface of the tubular portion.

17. The dental implement as claimed in claim 11, wherein the member is constructed of a molded plastic material.

18. A dental implement for the aspiration of fluids from a patient's mouth and for the retracting of soft tissues in said patient's mouth, the dental implement comprising a slender, elongate and substantially straight member having:
(a) a hollow tubular portion having a longitudinal axis and having a suction end and a connection end remote from the suction end for enabling the member to be connected to a suction tube or the like, the connection end of the tubular portion being round in transverse cross-section and an upper region of the tubular portion adjacent the suction end thereof being substantially flat so that the tubular portion is thinner at the suction end than at the connection end; and,
(b) first and second, longitudinally extending fins which project sidewardly from opposite, lower, side regions of said tubular portion, said fins being of substantially uniform width and being rigid and relatively narrow and extending along a substantial length of said tubular portion from the suction end thereof and extending around the suction end of the tubular portion so as to join one another at a vertical plane through said longitudinal axis, portions of the first and second fins around the suction end of the tubular portion being curved downwardly so as to form an arcuate, tissue-retraction tip of said member relatively adjacent the suction end of the tubular portion.

19. The dental implement as claimed in claim 18, wherein the suction end of the tubular portion is formed having an open end surface which is generally planar and is at an angle relative to a plane orthogonal to said longitudinal axis so that said open end surface at the flat upper region of the tubular portion is closer to said connection end than are other regions of said open end surface.

20. The dental implement as claimed in claim 18, wherein said first and second fins are of a substantially uniform thickness and wherein the width of each of the first and second fins is less than the outside diameter of the tubular portion at the connection end thereof.

21. The dental implement as claimed in claim 18, wherein the open end surface of the tubular portion suction end is formed having at least one recess to enable suction to be broken between said member and soft tissues of the patient's mouth.

22. The dental implement as claimed in claim 18, wherein all exposed edges of the tubular portion and the first and second fins are smoothly rounded so that there are no sharp exposed edges to cut a patient's mouth, and wherein upper and lower surfaces of the first and second fins are smoothly flared into the outer surface of the tubular portion.

23. The dental implement as claimed claim 18, wherein the member is constructed of a molded plastic material.

* * * * *